(12) United States Patent
Rix

(10) Patent No.: US 6,528,670 B1
(45) Date of Patent: Mar. 4, 2003

(54) BRIDGED METALLOCENES FOR OLEFIN COPOLYMERIZATION

(75) Inventor: Francis C. Rix, League City, TX (US)

(73) Assignee: ExxonMobil Chemical Patents Inc., Houston, TX (US)

(*) Notice: Subject to any disclaimer, the term of this patent is extended or adjusted under 35 U.S.C. 154(b) by 0 days.

(21) Appl. No.: 09/426,099

(22) Filed: Oct. 22, 1999

Related U.S. Application Data

(60) Provisional application No. 60/131,067, filed on Apr. 26, 1999, and provisional application No. 60/105,329, filed on Oct. 23, 1998.

(51) Int. Cl.$^7$ .............................. C07F 7/08; C07F 7/10
(52) U.S. Cl. ..................... 556/11; 526/126; 526/127
(58) Field of Search .................... 132/11; 526/126, 526/127

(56) References Cited

U.S. PATENT DOCUMENTS

| | | | |
|---|---|---|---|
| 4,892,851 A | 1/1990 | Ewen et al. | |
| 5,132,381 A | 7/1992 | Winter et al. | |
| 5,155,080 A | 10/1992 | Elder et al. | |
| 5,171,919 A | 12/1992 | Watanabe et al. | 585/523 |
| 5,225,501 A | 7/1993 | Fujita et al. | 526/127 |
| 5,324,800 A | 6/1994 | Welborn, Jr. et al. | |
| 5,369,196 A | 11/1994 | Matsumoto et al. | 526/127 |
| 5,401,817 A | 3/1995 | Palackal et al. | 526/127 |
| 5,407,882 A | 4/1995 | Yamada et al. | 502/114 |
| 5,408,017 A | 4/1995 | Turner et al. | |
| 5,502,017 A | 3/1996 | Marks et al. | |
| 5,616,663 A | 4/1997 | Imuta et al. | 526/127 |
| 5,688,735 A | 11/1997 | Ewen et al. | 502/117 |
| 5,767,208 A | 6/1998 | Turner et al. | |
| 5,770,664 A | 6/1998 | Okumura et al. | 526/127 |
| 5,770,666 A | 6/1998 | Hamura et al. | 526/134 |
| 5,859,272 A | 1/1999 | Imuta et al. | 556/11 |
| 6,169,051 B1 * | 1/2001 | Mitani et al. | 556/11 X |
| 6,171,994 B1 * | 1/2001 | Yabanouchi et al. | 556/11 X |
| 6,180,732 B1 * | 1/2001 | Ewen | 526/127 |
| 6,211,108 B1 * | 4/2001 | Bishop et al. | 556/11 X |
| 6,225,425 B1 * | 5/2001 | Dolle | 556/11 X |

FOREIGN PATENT DOCUMENTS

| | | |
|---|---|---|
| EP | 0 612 768 B1 | 8/1994 |
| EP | 0 612 769 B1 | 8/1994 |
| EP | 0 612 768 B1 | 11/1997 |
| EP | 0 612 769 B1 | 11/1997 |
| WO | WO 96/28480 | 9/1996 |

OTHER PUBLICATIONS

"Metallocenes",, Tosoh Corp, Polymerization, 1995, pp. 441–462.

"Synthesis and Applications of Metallocene–Based Elastomers" H. Miyata, et al, Presentation at MetCon'96, Jun. 12–13, 1996.

"Ethene/propene copolymerisation by [Me$_2$C(3–RCp)(Flu)]ZrCl$_2$/MAO (R—H, Me, $^{iso}$Pr, $^{tert}$Bu)", Arndt, et al, Macromol. Chem. Phys., vol. 199, 1998, pp. 1135–1152.

Ethylene/1–hexene copolymerization with Ph$_2$C(Cp)(Flu)-ZrCL$_2$ derivatives: correlation between ligand structure and copolymerization behavior at high temperature, Yano, et al, Macromol. Chem. Phys. vol. 200, pp. 1542–1553, 1999.

"Metallocenes," Tosoh Corp., Polymerization, pp. 441–462 (1995).

"Synthesis and Applications of Metallocene–Based Elastomers," H. Miyata, et al, Presentation at MetCon '96, Jun. 12–13, 1996.

"Ethene/propene Copolymerization by [Me2C(3–RCp)-(Flu)]ZrCl2/MAO(R–H, Me, isoPr,tertBu)", Arndt, et al, Macromol. Chem. Phys., vol. 199, 1998, pp. 1135–1152.

Ethelyne/l–hexene copolymerization with Ph2C(Cp)-(Flu)ZrCl2 derivatives: correlation between ligand structure and copolymerization behavior at high temperature, Yano, et al, Macromol. Chem. Phys. vol. 200, pp. 1542–1553, (1999).

"Synthesis of a dinuclear ansazirconocene catalyst having a biphenyl bridge and application to ethene polymerization", Soga, et al, J. Mol. Cat. A, 128, pp. 273–278, (1998), XP–000879084.

"Polymerization of Olefins with a Novel Dinuclear ansa–Zirconocene Catalyst Having a Biphenyl Bridge", Ban, et al, J. of Pol. Sci., Pol. Chem. Ed., US, John Wiley & Sons, NY, pp. 2269–2274, (1998).

"Polymerization process of olefins for polymers with broad molecular weight distribution and high catalytic activity", Chem. Abstracts, vol. 130, No. 1, (Jan. 4, 1999), XP—213–792 abstract.

* cited by examiner

Primary Examiner—Paul F. Shaver
(74) Attorney, Agent, or Firm—Frank E Reid; Charles Edwin Runyan, Jr.; William G. Muller

(57) ABSTRACT

The invention is directed to bridged metallocene catalyst complexes that are sufficiently soluble in aliphatic solvents to be particularly suitable for solution olefin polymerization processes such that olefin copolymers can be prepared with high molecular weights and catalyst activities particularly at high polymerization reaction temperatures. More specifically, the invention particularly relates to a polymerization process for ethylene copolymers having a density of about 0.850 to about 0.940 comprising contacting, under solution polymerization conditions at a reaction temperature at or above 60° C. to 250° C., ethylene and one or more comonomers capable of insertion polymerization with a bridged metallocene catalyst complex derived from two ancillary ligands, each of which independently may be substituted or unsubstituted, wherein the ligands are bonded by a covalent bridge containing a substituted single Group 14 atom, the substitution on said Group 14 atom comprising aryl groups at least one of which contains a hydrocarbylsilyl substituent; and B) an activating cocatalyst.

8 Claims, No Drawings

BRIDGED METALLOCENES FOR OLEFIN COPOLYMERIZATION

CROSS-REFERENCES TO RELATED APPLICATIONS

This application is related to the earlier filed provisional applications No. 60/105,329, filed Oct. 23, 1998 and No. 60/131,067 filed Apr. 26, 1999.

TECHNICAL FIELD

This invention relates to aryl-substituted-bridge containing organometallic catalyst compounds suitable for olefin polymerization processes.

BACKGROUND ART

Olefin polymers comprising ethylene and at least one or more α-olefin and optionally one or more diolefin make up a large segment of polyolefin polymers and will be addressed as "ethylene copolymers" herein. Such polymers range from crystalline polyethylene copolymers such as High Density Polyethylene with a density in excess of 0.94, to slightly crystalline polyethylene such as Linear Low Density Polyethylene with a density between 0.915 to 0.94, to largely amorphous elastomers with a density down to 0.85 and a relatively high molecular weight and with a new area of semi-crystalline "plastomers" with a density of between 0.915 and 0.86 and a moderate molecular weight. In particular, ethylene copolymer plastomers are now a well established class of industrial polymers having a variety of uses associated with their unique properties, such as elastomeric properties and their thermo-oxidative stability. Uses of the plastomers include general thermoplastic olefins, films, wire and cable coatings, polymer modification, injection molding, foams, footwear, sheeting, functionalized polymers and components in adhesive and sealant compounds.

Commercially prepared ethylene copolymers have been traditionally been made via Ziegler-Natta polymerization with catalyst systems largely based on vanadium or titanium. Newer metallocene catalyst compounds have received attention due to their ease of larger monomer incorporation and potential increases in polymerization activities. U.S. Pat. No. 5,324,800 describes metallocenes having substituted and unsubstituted cyclopentadienyl ligands which are suitable for producing high molecular weight olefin polymers, including linear, low density copolymers of ethylene with minor amounts of α-olefin.

The utility of bridged metallocene-based ionic catalysts in olefin polymerization is described in U.S. Pat. Nos. 5,408, 017 and 5,767,208, EP 0 612 768, and EP 0 612 769. Each addresses suitable bridged metallocene catalysts for high temperature processes for olefin copolymerization. Substituted single carbon, or methylene, bridging groups for metallocenes suitable as olefin polymerization catalysts is described in U.S. Pat. Nos. 4,892,851, 5,155,080 and 5,132, 381. Isopropylidene, mono- and diaryl methylene groups are identified as particularly suitable.

Olefin solution polymerization processes are generally conducted in aliphatic solvents that serve both to maintain reaction medium temperature profiles and solvate the polymer products prepared. However, aryl-group containing metallocenes, those having cyclopentadienyl derivatives and other fused or pendant aryl-group substituents, are at best sparingly soluble in such solvents and typically are introduced in aryl solvents such as toluene. Solution polymerization processes in aliphatic solvents thus can be contaminated with toluene that must be removed to maintain process efficiencies and to accommodate health-related concerns for both industrial manufacturing processes and polymer products from them. Alternatively, relatively insoluble catalysts can be introduced via slurry methods, but such methods required specialized handling and pumping procedures that complicate and add significant costs to industrial scale plant design and operation. Low solubility can also become disadvantageous should the process involve low temperature operation at some stage such as in typical adiabatic processes run in areas subject to low ambients temperatures. Additionally, separating or counteracting the build up in the recycle system of special catalyst solvents may become another problem. At the same time means of maintaining high molecular weights in olefin polymers while operating at economically preferable high polymerization reaction temperatures and high polymer production rates is highly desirable. It is therefore desirable to provide a metallocene catalyst which is active for polyethylene polymerization particularly at elevated temperatures which nevertheless has increased solubility in aliphatic solvents.

BRIEF SUMMARY OF THE INVENTION

The invention thus addresses specifically substituted, bridged metallocene catalyst complexes comprising a solubilizing covalent bridge comprising at least one hydrocarbylsilyl substitutent. It can be described as a Group 4 organometallic compound comprising two ancillary monanionic ligands, each of which independently may be substituted or unsubstituted, wherein the ligands are bonded by a covalent bridge containing a substituted single Group 14 atom, the substitution on said Group 14 atom comprising aryl groups at least one of which contains at least one hydrocarbylsilyl substituent group sufficient to provide increased solubility in aliphatic solvents. Additionally, the invention relates to solution polymerization processes for ethylene copolymers having a density of about 0.850 to about 0.940 comprising contacting, under supercritical or solution polymerization conditions at reaction temperatures of 40° C. to 300° C., ethylene and one or more comonomers capable of insertion polymerization with a metallocene catalyst complex derived from A) a metallocene compound having a covalent bridge connecting a cyclopentadienyl ligand to another ancillary anionic metal ligand group, said bridge containing a substituted single Group 14 atom, the substitution on said Group 14 comprising aryl groups at least one of which contains at least one hydrocarbylsilyl substituent group of the formula $R^2_n SiR^1_{3-n}$, where each $R^1$ is independently a $C_1-C_{20}$ hydrocarbyl, hydrocarbylsilyl, hydrofluorocarbyl substituent, $R^2$ is a $C_1-C_{10}$ linking group between Si and the aryl group, and n=0, 1 or 2. Where n=0, the Si atom is covalently bound directly to an aryl group ring carbon atom.

DETAILED DESCRIPTION OF THE INVENTION

The bridged metallocene compounds of the invention are those having a single substituted carbon or silicon atom bridging two ancillary monanionic ligands, such as substituted or unsubstituted cyclopentadienyl-containing (Cp) ligands and/or substituted and unsubstituted Group 13–16 heteroatom ligands, of the metallocene metal centers. The bridge substituents are substituted aryl groups, the substituents including at least one solubilizing hydrocarbylsilyl substituent located on at least one of the aryl group bridge substituents. Substituents present on the cyclopentadienyl and/or heteroatom ligands include $C_1$–$C_{30}$ hydrocarbyl, hydrocarbylsilyl or hydrofluorocarbyl groups as replacements for one or more of the hydrogen groups on those ligands, or those on fused aromatic rings on the cyclopentadienyl rings. Aromatic rings can be substituents on cyclopentadienyl ligand and are inclusive of the indenyl and fluorenyl derivatives of cyclopentadienyl groups, and their hydrogenated counterparts. Such typically may include one or more aromatic ring substituent selected from linear, branched, cyclic, aliphatic, aromatic or combined structure groups, including fused-ring or pendant configurations. Examples include methyl, isopropyl, n-propyl, n-butyl, isobutyl, tertiary butyl, neopentyl, phenyl, n-hexyl, cyclohexyl, benzyl, and adamantyl. For the purposes of this application the term "hydrocarbon" or "hydrocarbyl" is meant to include those compounds or groups that have essentially hydrocarbon characteristics but optionally contain not more than about 10 mol. % non-carbon heteroatoms, such as boron, silicon, oxygen, nitrogen, sulfur and phosphorous. Additionally, the term is meant to include hydrofluorocarbyl substitutent groups. "Hydrocarbylsilyl" is exemplified by, but not limited to, dihydrocarbyl- and trihydrocarbylsilyls, where the preferred hydrocarbyl groups are preferably $C_1$–$C_{30}$ substituent hydrocarbyl, hydrocarbylsilyl or hydrofluorocarbyl substitutents for the bridging group phenyls. For heteroatom containing catalysts see WO 92/00333. Also, the use of hetero-atom containing rings or fused rings, where a non-carbon Group 13, 14, 15 or 16 atom replaces one of the ring carbons is considered for this specification to be within the terms "cyclopentadienyl", "indenyl", and "fluorenyl". See, for example, the background and teachings of WO 98/37106, having common priority with U.S. Ser. No. 08/999,214, filed Dec. 29, 1997, and WO 98/41530, having common priority with U.S. Ser. No. 09/042,378, filed Mar. 13, 1998, both incorporated by reference for purposes of U.S. patent practice.

These compounds can be generically represented as illustrated below:

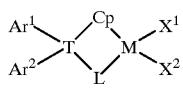

where Cp is a substituted or unsubstituted cyclopentadienyl-containing ancillary ligand, L is independently selected from Cp ligands as previously defined, or is a substituted or unsubstituted Group 13–16 heteroatom ligand, T is a Group 14 element-containing bridging group, $AR^1$ and $Ar^2$ are the substituted aryl groups which may be the same or different, M is a Group 3–6 metal, and $X^1$ and $X^2$ are the same or different labile ligands capable of being abstracted for activation and suitable for olefin insertion, or capable of alkylation so as to be abstractable and suitable for olefin insertion. The term "ancillary ligand" is being used to refer to bulky monoanioic ligands that stabilize the metal center to which bonded against oxidative reaction (i.e., debonding of the ligand by chemical reaction) and the term "labile ligand" refers to ligands which may be readily replaced, abstracted, or removed from the metal center to which bonded.

For illustration purposes $Ar^1$ and Ar2 may be independently selected from the groups below:

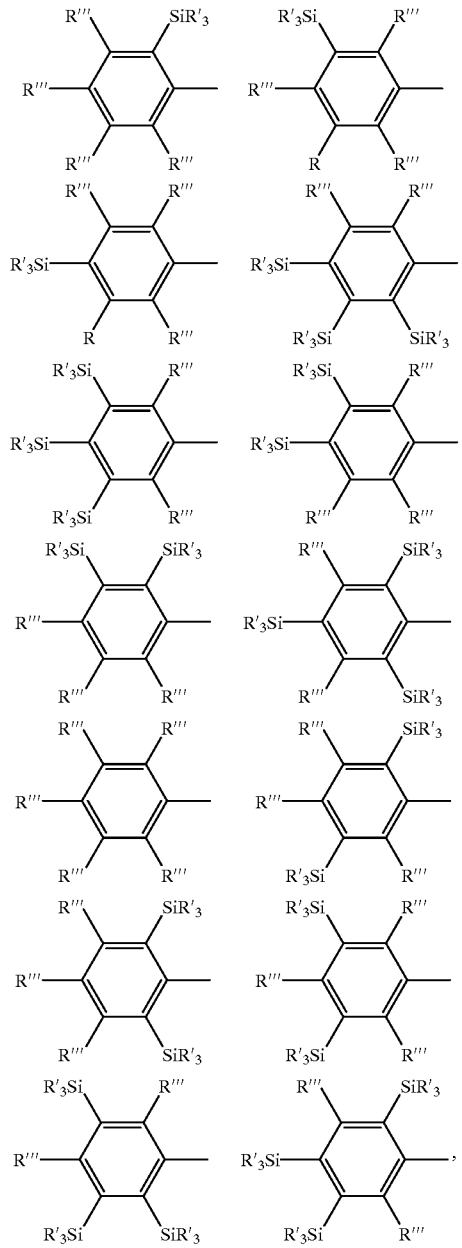

where any R' is independently any of the groups below except H and any R''' is independently any of the groups below:

| | | | |
|---|---|---|---|
| H | $CH(CH_3)_2$ | $C_4H_7$ | $CH_2CH=CH_2$ |
| $CH_3$ | $CH_2CH(CH_3)_2$ | $C_5H_9$ | $CH_2CH_2CH=CH_2$ |
| $CH_2CH_3$ | $CH_2CH_2CH(CH_3)_2$ | $C_6H_{11}$ | $CH_2CH_2(CF_2)_7CF_3$ |
| $CH_2CH_2CH_3$ | $C(CH_3)_2CH(CH_3)_2$ | $C_7H_{13}$ | $CF_3$ |
| $CH_2(CH_2)_2CH_3$ | $CH(C(CH_3)_3)CH(CH_3)_2$ | $C_8H_{15}$ | $N(CH_3)_2$ |

| -continued | | | |
|---|---|---|---|
| CH$_2$(CH$_2$)$_{3-30}$CH$_3$ | C(CH$_3$)$_3$ | C$_9$H$_{17}$ | N(C$_2$H$_5$)$_2$ |
| CH$_2$C(CH$_3$)$_3$ | CH$_2$Si(CH$_3$)$_3$ | C$_6$H$_5$ | OC(CH$_3$)$_3$ |
| CH=CH$_2$ | CH$_2$Ph | CH$_2$SiR$_3$ | |

Cp and L, independently, may be any of ligands below where R''' is as shown above.

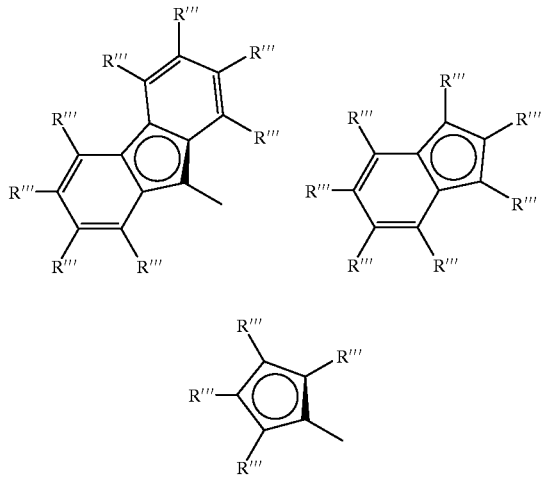

X$^1$ and X$^2$ may independently be any of the groups listed for R''' plus any of Cl, Br, I, —NHR''', —N(R''')$_2$, or —OR'''. X$^1$ and X$^2$ may additionally be linked together so as to form a bidentate ligand such as cycloaliphatic hydrocarbyl bidentate ligand or cycloalkenyl hydrocarbyl ligand.

An illustrative representative is

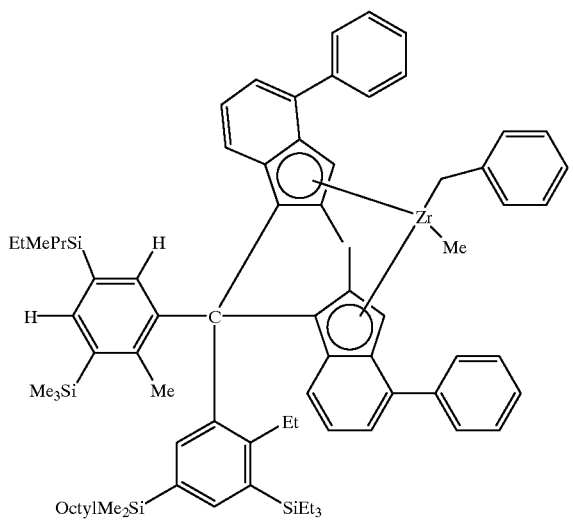

where Me is methyl, Et is ethyl and Octyl is octyl.

Specific exemplary bridged hafnium catalysts include those derived from: indenyl-based complexes such as the isomers, or mixtures, of di(para-triethylsilyl-phenyl) methylene bis(indenyl) hafnium dimethyl, di(para-trimethylsilyl-phenyl)methylene bis(indenyl) hafnium dimethyl, of di(para-tri-n-propylsilyl-phenyl)methylene bis (indenyl)hafnium dimethyl, (para-triethylsilyl-phenyl)(para-t-butylphenyl)methylene(fluorenyl) (indenyl) hafnium dimethyl, (para-triethylsilyl-phenyl)(para-methylphenyl) methylene (fluorenyl)(indenyl)hafnium dimethyl, di(para-triethylsilyl-phenyl)methylene(2,7-di tertbutyl fluorenyl) (indenyl)hafnium dimethyl, (para-trimethylsilyl-phenyl) (para-n-butylphenyl)methylene (2,7-di tertbutyl fluorenyl) (indenyl) hafnium dimethyl, (para-triethylsilyl-phenyl) (para-n-butylphenyl)methylene bis(tetrahydroindenyl) hafnium dibenzyl and di(para-triethylsilyl-phenyl) methylene bis(tetrahydroindenyl)hafnium dimethyl.

Similarly, exemplary zirconium compounds include di(para-triethylsilyl-phenyl)methylene bis(indenyl) zirconium dimethyl, di(para-trimethylsilyl-phenyl) methylene bis(indenyl)zirconium dimethyl, of di(para-tri-n-propylsilyl-phenyl)methylene bis(indenyl)zirconium dimethyl, (para-triethylsilyl-phenyl)(para-t-butylphenyl) methylene(fluorenyl) (indenyl)zirconium dimethyl, (para-triethylsilyl-phenyl)(para-methylphenyl)methylene (fluorenyl)(indenyl)zirconium dimethyl, di(para-triethylsilyl-phenyl)methylene(2,7-di tertbutyl fluorenyl) (indenyl)zirconium dimethyl, (para-trimethylsilyl-phenyl) (para-n-butylphenyl)methylene (2,7-di tertbutyl fluorenyl) (indenyl)zirconium dimethyl, (para-triethylsilyl-phenyl) (para-n-butylphenyl)methylene bis(tetrahydroindenyl) zirconium dibenzyl and di(para-triethylsilyl-phenyl) methylene bis(tetrahydroindenyl)zirconium dimethyl. Additional preferred zirconium metallocenes useful when prepared with the solubilizing bridging groups in accordance with this invention are those described in copending U.S. application Ser. No. 09/251,819, filed Feb. 17, 1999, and equivalent WO 99/41294, these catalyst structures and the solution polymerization process described with them are particularly suited for this invention, and are incorporated by reference for purposes of U.S. patent practice.

Particularly suitable cyclopentadienyl-based complexes are the compounds, isomers, or mixtures, of (para-trimethylsilylphenyl)(para-n-butylphenyl)methylene (fluorenyl)(cyclopentadienyl)hafnium dimethyl, di(para-trimethylsilylphenyl)methylene(2,7-di-tertbutyl fluorenyl) (cyclopentadienyl)hafnium dimethyl, di(para-trimethylsilylphenyl)methylene(2,7-di-tertbutyl-fluorenyl) (cyclopentadienyl)hafnium dimethyl, (para-trimethylsilylphenyl)(para-t-butylphenyl)methylene(2,7-di tertbutyl fluorenyl)(cyclopentadienyl)hafnium dimethyl or dibenzyl, and di(para-trimethylsilylphenyl)methylene(2,7-dimethylfluorenyl)(cyclopentadienyl)hafnium dimethyl or dibenzyl. The zirconocene analogues are (para-trimethylsilylphenyl)(para-n-butylphenyl)methylene (fluorenyl)(cyclopentadienyl)zirconium dimethyl, di(para-trimethylsilylphenyl)methylene(2,7-di-tertbutyl fluorenyl) (cyclopentadienyl)zirconium dimethyl, di(para-trimethylsilylphenyl)methylene(2,7-di-tertbutyl-fluorenyl) (cyclopentadienyl)zirconium dimethyl, (para-trimethylsilylphenyl)(para-t-butylphenyl)methylene(2,7-di tertbutyl fluorenyl)(cyclopentadienyl)zirconium dimethyl or dibenzyl, and di(para-triethylsilyl-phenyl)methylene(2,7-dimethylfluorenyl)(cyclopentadienyl)zirconium dimethyl or dibenzyl. It has been found that the substituted bridge-containing compounds, such as those asymmetric compounds listed above, are particularly useful in accordance with the invention.

In particular, for the bridged metallocene compounds, increasing the degree of substitution on an aromatic fused-ring substituted ligand Cp can be effective for increased molecular weight, e.g., 2,7-dimethyl-fluorenyl, 2,7-di-tert-butyl-fluorenyl and 2,7-methyl-phenyl-fluorenyl groups are exemplary of such. Preferably substitution on fluorenyl or indenyl radicals (ii) in the metallocene compounds will generally comprise two or more $C_1$ to $C_{30}$ hydrocarbyl or hydrocarbylsilyl replacements, or substitutions, for a ring hydrogen of at least one 6-member fused-ring, preferably both where a fluorenyl radical.

The bridged metallocene compounds according to the invention may be activated for polymerization catalysis in any manner sufficient to allow coordination or cationic polymerization. This can be achieved for coordination polymerization when one ligand can be abstracted and another will either allow insertion of the unsaturated monomers or will be similarly abstractable for replacement with a ligand that allows insertion of the unsaturated monomer (labile ligands), e.g., alkyl, silyl, or hydride. The traditional activators of coordination polymerization art are suitable, those typically include Lewis acids such as alumoxane compounds, and ionizing, anion precursor compounds that abstract one so as to ionize the bridged metallocene metal center into a cation and provide a counter-balancing noncoordinating anion.

Alkylalumoxanes and modified alkylalumoxanes are suitable as catalyst activators, particularly for the invention metal compounds comprising halide ligands. The alumoxane component useful as catalyst activator typically is an oligomeric aluminum compound represented by the general formula $(R''-Al-O)_n$, which is a cyclic compound, or $R''(R''-Al-O)_nAlR''_2$, which is a linear compound. In the general alumoxane formula R" is independently a $C_1$ to $C_{10}$ alkyl radical, for example, methyl, ethyl, propyl, butyl or pentyl and "n" is an integer from 1 to about 50. Most preferably, R" is methyl and "n" is at least 4. Alumoxanes can be prepared by various procedures known in the art. For example, an aluminum alkyl may be treated with water dissolved in an inert organic solvent, or it may be contacted with a hydrated salt, such as hydrated copper sulfate suspended in an inert organic solvent, to yield an alumoxane. Generally, however prepared, the reaction of an aluminum alkyl with a limited amount of water yields a mixture of the linear and cyclic species of the alumoxane. Methylalumoxane and modified methylalumoxanes are preferred. For further descriptions see, U.S. Pat. Nos. 4,665,208, 4,952,540, 5,041,584, 5,091,352, 5,206,199, 5,204,419, 4,874,734, 4,924,018, 4,908,463, 4,968,827, 5,329,032, 5,248,801, 5,235,081, 5,157,137, 5,103,031 and EP 0 561 476 A1, EP 0 279 586 B1, EP 0 516 476 A, EP 0 594 218 A1 and WO 94/10180, each being incorporated by reference for purposes of U.S. patent practice.

When the activator is an alumoxane, the preferred transition metal compound to activator molar ratio is from 1:2000 to 10:1, more preferably from about 1:500 to 10:1, even more preferably from about 1:250 to 1:1 and most preferably from about 1:100 to 1:1.

The term "noncoordinating anion" is recognized to mean an anion which either does not coordinate to the metal cation or which is only weakly coordinated to it thereby remaining sufficiently labile to be displaced by a neutral Lewis base, such as an olefinically or acetylenically unsaturated monomer. Any complex capable of counterbalancing a cationic charge without impeding or interfering with olefin polymerization, including both being incapable of reacting with metallocene cations so as to render them neutral and remaining sufficiently labile so as to be replaceable at the polymerization site by olefin monomers, will be suitable in accordance with the invention. Typically such complexes are based on ionic salts or neutral Lewis acids of the Group 8–14 metalloid or metal elements, particularly boron or aluminum having substituted aryl groups that are substituted so as to present steric or electronic impediments to oxidation of the complexes by reaction of the transition metal center with the aryl groups bonded to the Group 13 atoms. Zwitterionic complexes of Group 13 elements comprising both catonic and anionic charges where meeting the functional requisites above are additionally suitable.

Additional suitable anions are known in the art and will be suitable for use with the metallocene catalysts of the invention. See in particular, U.S. Pat. No. 5,278,119 and the review articles by S. H. Strauss, "The Search for Larger and More Weakly Coordinating Anions", *Chem. Rev.*, 93, 927–942 (1993) and C. A. Reed, "Carboranes: A New Class of Weakly Coordinating Anions for Strong Electrophiles, Oxidants and Superacids", *Acc. Chem. Res.*, 31, 133–139 (1998).

Specific descriptions of ionic catalysts, those comprising a transition metal cation and a noncoordinating anion, suitable for coordination polymerization appear in the U.S. Pat. Nos. 5,064,802, 5,132,380, 5,198,401, 5,278,119, 5,321,106, 5,347,024, 5,408,017, 5,599,671, and international publications WO 92/00333, WO 93/14132 and WO 97/35893. These teach a preferred method of preparation wherein metallocenes are protonated by noncoordinating anion precursors such that an alkyl, alkenyl or hydride group is abstracted by protonation from a transition metal to make it both cationic and charge-balanced by the noncoordinating anion.

The use of ionizing ionic compounds not containing an active proton but capable of producing both the metallocene cation and an noncoordinating anion is also useful. See, EP-A-0 426 637, EP-A-0 573 403 and U.S. Pat. No. 5,387,568 for instructive ionic compounds. Reactive cations of the ionizing ionic compounds, other than the Bronsted acids, include ferrocenium, silver, tropylium, triphenylcarbenium and triethylsilylium, or alkali metal or alkaline earth metal cations such as sodium, magnesium or lithium cations. A further class of noncoordinating anion precursors suitable in accordance with this invention are hydrated salts comprising the alkali metal or alkaline earth metal cations and a noncoordinating anion as described above. The hydrated salts can be prepared by reaction of the metal cation-noncoordinating anion salt with water, for example, by hydrolysis of the commercially available or readily synthesized $LiB(pfp)_4$ which yields $[Li.xH_2O][B(pfp)_4]$, where (pfp) is pentafluorophenyl or perfluorophenyl.

Any metal or metalloid capable of forming a coordination complex which is resistant to degradation by water (or other Bronsted or Lewis Acids) may be used or contained in the noncoordinating anion. Suitable metals include, but are not limited to, aluminum, gold, platinum and the like. Suitable metalloids include, but are not limited to, boron, phosphorus, silicon and the like. The description of noncoordinating anions and precursors thereto of the documents of the foregoing paragraphs are incorporated by reference for purposes of U.S. patent practice.

An additional method of making the active polymerization catalysts of this invention uses ionizing anion precursors which are initially neutral Lewis acids but form a metallocene cation and the noncoordinating anion upon ionizing reaction with the invention compounds, for example tris(pentafluorophenyl) boron acts to abstract a hydrocarbyl, hydride or silyl ligand to yield a metallocene cation and stabilizing noncoordinating anion, see EP-A-0 427 697 and EP-A-0 520 732 for illustration. See also the methods and compounds of EP-A-0 495 375. The description of noncoordinating anions and precursors thereto of these documents are similarly incorporated by reference for purposes of U.S. patent practice.

When the $X_1$ and $X_2$ labile ligands are not hydride, hydrocarbyl or silylhydrocarbyl, such as chloride, amido or alkoxy ligands and are not capable of discrete ionizing abstraction with the ionizing, anion pre-cursor compounds, these X ligands can be converted via known alkylation reactions with organometallic compounds such as lithium or aluminum hydrides or alkyls, alkylalumoxanes, Grignard reagents, etc. See EP-A-0 500 944, EP-A1-0 570 982 and EP-A1-0 612 768 for analogous processes describing the reaction of alkyl aluminum compounds with dihalide substituted metallocene compounds prior to or with the addition of activating noncoordinating anion precursor compounds.

Preferred invention activating cocatalyst, precursor ionizing compounds comprise Group 13 element complexes having at least two halogenated aromatic ligands such as the halogenated tetraphenyl boron and aluminum compounds exemplified in the identified prior art. Preferred aromatic ligands consist of the readily available phenyl, and polycyclic aromatic hydrocarbons and aromatic ring assemblies in which two or more rings (or fused ring systems) are joined directly to one another or together. These ligands, which may be the same or different, are covalently bonded directly to the metal/metalloid center. In a preferred embodiment the aryl groups are halogenated, preferably fluorinated, tetraaryl Group 13 element anionic complexes comprising at least one fused polycyclic aromatic hydrocarbon or pendant aromatic ring. The halogenated ligands are also represented by those aryl ligands having flourinated alkyl groups. Indenyl, napthyl, anthracyl, heptalenyl and biphenyl ligands are exemplary aryl ligands. See co-pending application U.S. Ser. No. 09/261,627, filed Mar. 3, 1999, and equivalent WO 99/45042, incorporated by reference for the purposes of U.S. patent practice.

Particularly preferred cocatalyst complexes for solution polymerization processes are those which are soluble in aliphatic solvents, whether by virtue of substitution on the Group 13 element ligands or substitution on precursor cations, see for example U.S. Pat. No. 5,502,017 and WO 97/35893. When the cation portion of an ionic noncoordinating anion precursor is a Bronsted acid such as protons or protonated Lewis bases (excluding water), or a reducible Lewis acid such as ferrocenium or silver cations, or alkaline metal or alkaline earth metal cations such as those of sodium, magnesium or lithium cations, the transition metal to activator molar ratio may be any ratio, but preferably from about 10:1 to 1:10, more preferably from about 5:1 to 1:5, even more preferably from about 2:1 to 1:2 and most preferably from about 1.2:1 to 1:1.2 with the ratio of about 1:1 being the most preferred.

Thus suitable active catalyst complexes for coordination and carbocationic polymerization can be prepared by activation with the traditional metallocene activators, typically alkylalumoxanes and ionizing haloaryl boron or aluminum compounds known in the art. The active catalysts thus are catalytically active components comprising complexes derived from the invention metallocene compounds containing the solubilizing bridge binding together the ancillary ligands according to the invention, and activating cocatalyst compounds.

The catalyst complexes of the invention are useful in polymerization of unsaturated monomers conventionally known to be polymerizable under either coordination polymerization conditions or cationic polymerization conditions. Such conditions are well known and include solution polymerization, supercritical phase polymerization, slurry polymerization, and low, medium and high pressure gas-phase polymerization. The catalyst of the invention may be supported and as such will be particularly useful in the known operating modes employing fixed-bed, moving-bed, fluid-bed, or slurry processes conducted in single, series or parallel reactors, with the added benefit that increased solubility will be useful in catalyst synthesis processes where the introduction of toluene is to be reduced or slurry pump introduction means to be avoided.

When using the catalysts of the invention, the total catalyst system will generally additionally comprise one or more organometallic compound. Such compounds as used in this application and its claims is meant to include those compounds effective for removing polar impurities from the reaction environment and for increasing catalyst activity. Impurities can be inadvertently introduced with any of the polymerization reaction components, particularly with solvent, monomer and catalyst feed, and adversely affect catalyst activity and stability. It can result in decreasing or even elimination of catalytic activity, particularly when ionizing anion pre-cursors activate the catalyst system. The polar impurities, or catalyst poisons include water, oxygen, metal impurities, etc. Preferably steps are taken before provision of such into the reaction vessel, for example by chemical treatment or careful separation techniques after or during the synthesis or preparation of the various components, but some minor amounts of organometallic compound will still normally be used in the polymerization process itself.

Typically these compounds will be organometallic compounds such as the Group 13 organometallic compounds of U.S. Pat. Nos. 5,153,157, 5,241,025 and WO-A-91/09882, WO-A-94/03506, WO-A-93/14132, and that of WO 95/07941. Exemplary compounds include triethyl aluminum, triethyl borane, triisobutyl aluminum, methylalumoxane, and isobutyl aluminumoxane. Those compounds having bulky or $C_6-C_{20}$ linear hydrocarbyl substituents covalently bound to the metal or metalloid center being preferred to minimize adverse interaction with the active catalyst. Examples include triethylaluminum, but more preferably, bulky compounds such as triisobutylaluminum, trisoprenylaluminum, and long-chain linear alkyl-substituted aluminum compounds, such as tri-n-hexylaluminum, tri-n-octylaluminum, or tri-n-dodecylaluminum. When alumoxane is used as activator, any excess over the amount needed to activate the catalysts present can act as a poison scavenger compound and additional organometallic compounds may not be necessary. Alumoxanes also may be used in scavenging amounts with other means of activation, e.g., methylalumoxane and trisobutyl-aluminoxane with boron-based activators. The amount of such compounds to be used with catalyst compounds of the inventions is minimized during polymerization reactions to that amount effective to enhance activity (and with that amount necessary for activation of the catalyst compounds if used in a dual role) since excess amounts may act as catalyst poisons.

In preferred embodiments of the process for this invention, the catalyst system is employed in liquid phase (solution, slurry, suspension, bulk phase or combinations thereof), in high pressure liquid or supercritical fluid phase.

Each of these processes may be employed in singular, parallel or series reactors. The liquid processes comprise contacting olefin monomers with the above described catalyst system in a suitable diluent or solvent and allowing said monomers to react for a sufficient time to produce the invention copolymers. Aliphatic solvents and mixed aliphatic solvents are industrially suitable for solution processes, and are particularly preferred.

The process of the invention is especially applicable to homogeneous solution polymerization which is also substantially adiabatic, that is to say the heat of polymerization is accommodated by a rise in temperature of the polymerization reactor contents, here principally solvent. This adiabatic process typically has no internal cooling and suitably no external cooling. The reactor outlet stream removes the heat of polymerization from the reactor. The productivity of such adiabatic processes can be improved by cooling the inlet solvent and/or monomer stream(s) prior to introduction into the reactor to permit a greater polymerization exotherm. Thus the catalyst, cocatalyst and scavenger selections disclosed in this application can be advantageously practiced in a continuous, solution process operated at or above 140° C., above 150° C. or above 160° C., up to about 250° C. Typically this process is conducted in an inert hydrocarbon solvent, linear, cyclic or branched aliphatic, or aromatic, at a pressure of from 20 to 200 bar. These catalysts' ability to provide a commercially desirable polymer at elevated temperatures contributes to a greater exotherm, to high polymer contents in the reactor because of lower viscosity, and to reduced energy consumption in evaporating and recycling solvent, and better monomer and comonomer conversions. See, for example, U.S. Pat. No. 5,767,208, and co-pending U.S. application Ser. No. 09/261,637, filed March 3, 1999, and its equivalent WO 99/45041, all of which are incorporated by reference for purposes of U.S. patent practice.

The catalyst according to the invention may be supported for use in gas phase, bulk, slurry polymerization processes, or otherwise as needed. Numerous methods of support are known in the art for copolymerization processes for olefins, any is suitable for the invention process in its broadest scope. See, for example, alumoxane activated catalysts of U.S. Pat. Nos. 5,057,475 and 5,227,440. An example of supported ionic catalysts appears in WO 94/03056. Particularly effective methods for ionic catalysts are that described in U.S. Pat. Nos. 5,427,991, 5,647,847 and WO 98/55518. A bulk, or slurry, process utilizing supported, invention metallocene compounds activated with alumoxane co-catalysts can be utilized as described for ethylene-propylene rubber in U.S. Pat. Nos. 5,001,205 and 5,229,478, these processes will additionally be suitable with the catalyst systems of this application. Both inorganic oxide and polymeric supports may be utilized in accordance with the knowledge in the field. See U.S. Pat. Nos. 5,422,325, 5,427,991, 5,498,582, 5,466,649, copending U.S. patent applications Ser. Nos. 08/265,532 and 08/265,533, both filed Jun. 24, 1995, and international publications WO 93/11172 and WO 94/07928. Each of the foregoing documents is incorporated by reference for purposes of U.S. patent practice.

Bulk and slurry processes are typically done by contacting the catalysts with a slurry of liquid monomer or diluent, the catalyst system being supported. Gas phase processes typically use a supported catalyst and are conducted in any manner known to be suitable for ethylene homopolymers or copolymers prepared by coordination polymerization. Illustrative examples may be found in U.S. Pat. Nos. 4,543,399, 4,588,790, 5,028,670, 5,382,638, 5,352,749, 5,436,304, 5,453,471, and 5,463,999, and WO 95/07942. Each is incorporated by reference for purposes of U.S. patent practice.

Generally speaking the polymerization reaction temperature can vary from about −50° C. to about 300° C. Preferably the reaction temperature conditions will be from −20° C. to 250°, and most advantageously in high temperature, adiabatic solution processes from and including about 120° C. to including and about 230° C. The pressure can vary from about 1 mm Hg to 2500 bar, preferably from 0.1 bar to 1600 bar, most preferably from 1.0 to 500 bar.

Ethylene-α-olefin (including ethylene-cyclic olefin and ethylene-α-olefin-diolefin) elastomers of high molecular weight and low crystallinity can be prepared utilizing the catalysts of the invention under traditional solution polymerization processes (above) or by introducing ethylene gas into a slurry utilizing the α-olefin or cyclic olefin or mixture thereof with other monomers, polymerizable and not, as a polymerization diluent in which the invention catalyst is suspended. Typical ethylene pressures will be between 10 and 1000 psig (69–6895 kPa) and the polymerization diluent temperature will typically be between −10–160° C. The process can be carried out in a stirred tank reactor or tubular reactor, or more than one operated in series or parallel. See the general disclosure of U.S. Pat. No. 5,001,205 for general process conditions. All documents are incorporated by reference for description of polymerization processes, ionic activators and useful scavenging compounds.

Pre-polymerization of the supported catalyst of the invention may also be used for further control of polymer particle morphology in typical slurry or gas phase reaction processes in accordance with conventional teachings. For example such can be accomplished by pre-polymerizing a $C_2$–$C_6$ alpha-olefin for a limited time, for example, ethylene is contacted with the supported catalyst at a temperature of −15 to 30° C. and ethylene pressure of up to about 250 psig (1724 kPa) for 75 min. to obtain a polymeric coating on the support of polyethylene of 30,000–150,000 molecular weight. The pre-polymerized catalyst is then available for use in the polymerization processes referred to above. The use of polymeric resins as a support coating may additionally be utilized, typically by suspending a solid support in dissolved resin of such material as polystyrene with subsequent separation and drying. All documents are incorporated by reference for description of metallocene compounds, ionic activators and useful scavenging compounds.

Other olefinically unsaturated monomers besides those specifically described above may be polymerized using the catalysts according to the invention by coordination polymerization, for example, styrene, alkyl-substituted styrenes, ethylidene norbornene, vinyl norbornene, norbornadiene, dicyclopentadiene, and other olefinically-unsaturated monomers, including other cyclic olefins, such as cyclopentene, norbornene, and alkyl-substituted norbornenes. Additionally, alpha-olefinic macromonomers of up to 300 mer units, or more, may also be incorporated by copolymerization.

The following examples are presented to illustrate the foregoing discussion. All parts, proportions and percentages are by weight unless otherwise indicated. All examples were carried out in dry, oxygen-free environments and solvents. Although the examples may be directed to certain embodiments of the present invention, they are not to be viewed as limiting the invention in any specific respect. In these examples certain abbreviations are used to facilitate the description. These include standard chemical abbreviations for the elements and certain commonly accepted abbreviations, such as Me=methyl, Et=ethyl, t-Bu=tertiary-butyl, Oct=octyl, Cp=cyclopentadienyl, Ind=indenyl, Flu=fluorenyl, THF (or thf)=tetrahydrofuran, Ph=phenyl, and pfp=pentafluorophenyl.

All molecular weights are weight average molecular weight unless otherwise noted. Molecular weights (weight average molecular weight (Mw) and number average molecular weight (Mn) were measured by Gel Permeation Chromatography, unless otherwise noted, using a Waters 150 Gel Permeation Chromatograph equipped with a differential refractive index (DRI) and low angle light scattering (LS) detectors and calibrated using polystyrene standards. Samples were run in 1,2,4-trichlorobenzene (135° C.) using three Polymer Laboratories PC Gel mixed B columns in series. This general technique is discussed in "Liquid Chromatography of Polymers and Related Materials III" J. Cazes Ed., Marcel Decker, 1981, page 207, which is incorporated by reference for purposes of U.S. patent practice herein. No corrections for column spreading were employed; however, data on generally accepted standards, e.g. National Bureau of Standards Polyethylene 1475, demonstrated a precision with 0.2 units for Mw/Mn which was calculated from elution times.

EXAMPLES

Synthesis of (p-Et$_3$Si-phenyl)$_2$C(2,7-$^t$Bu$_2$Flu)(Cp)HfMe$_2$ (Catalyst A)

1. Synthesis of 1-Br,4-(Et$_3$Si)benzene

To a cold (−78° C.) slurry of 1,4-dibromobenzene (235 g, 0.99 mol) and anhydrous THF (1.5 L) was added a solution of nBuLi (1.0 mol), pentane (300 mL) and ether (100 mL). After stirring for 3 h, Et$_3$SiCl (150 g, 1.0 mol) was added. The mixture was allowed to slowly warm to room temperature, stirred for a total of ca. 60 h. then quenched with water (50 mL). The organic layer was separated, washed with additional water (2×50 mL), dried over MgSO$_4$, filtered, then reduced to an orange oil. Vacuum distillation (60 mtorr) gave product (bp 83° C.). Yield 124 g, 46%.

2. Synthesis of 6,6'-bis(p-Et$_3$Si-phenyl)fulvene

To a cold (−78° C.) slurry of 1-Br,4-(Et$_3$Si)benzene (124 g, 0.46 mol) and anhydrous THF (0.5 L) was added a solution of nBuLi (0.46 mol) and pentane (246 mL). After stirring for 75 min, ClC(O)NMe$_2$ (21 mL, 0.23 mol) was added. The mixture was slowly warmed to room temperature overnight then cooled in an ice bath. Cyclopentadiene (46 mL, 0.55 mol) was added then the color soon turned red. After stirring in an ice bath for 8 h, the mixture was warmed to room temperature overnight. The mixture was extracted with water (4×100 mL) in two stages (tot. 800 mL water), dried with MgSO$_4$ then reduced to an oil. The oil was taken up in ether (200 mL), dried with CaH$_2$, filtered, then reduced to a red oil. Yield of crude product 114.8 g.

3. Synthesis of (p-Et$_3$Si-phenyl)$_2$C(2,7-$^t$Bu$_2$Fu)(Cp)HfCl$_2$ 2,7-$^t$Bu$_2$fluorenyl lithium (69.5 g, 0.25 mol) was added to a cooled (−30° C.) solution of the crude fulvene (114.8 g, 0.25 mol) and ether (500 mL). The mixture was warmed to room temperature overnight then reduced to an orange oil. Addition of pentane (0.5 L) caused a slurry to form. Filtration, pentane washing (2×100 mL) and drying yielded p-Et$_3$Si-phenyl)$_2$C(2,7-$^t$Bu$_2$FluH)(CpLi) as a white solid (97 g, 53%—assuming no ether present). 2 M BuLi in pentane (64.5 mL, 0.129 mol) was added to a slurry of the monoanion (95 g, 0.129 mol) and ether (1 L). After stirring overnight, the orange mixture was cooled to −30° C. then treated with HfCl$_4$ (41.4 g, 1 equiv.). The mixture was warmed to room temperature, stirred for 24 h then reduced to a solid in vacuo. The solids were extracted with methylene chloride (500 mL total) then filtered through Celite. The filtrate was reduced to a solid, extracted with pentane (3×100 mL) then dried. The product was extracted from the solids with a mixture of toluene and hexane (1:1) at 60° C. then filtered through a 0.45 μm filter. Removing the solvent gave product. Yield 70 g, 55%.

4. Synthesis of (p-Et$_3$Si-phenyl)$_2$C(2,7-$^t$Bu$_2$Flu)(Cp)HfMe$_2$ (Catalyst A)

A 1.4 M solution of MeLi in ether (21.8 mL, 30.5 mmol) was added to a solution of (p-Et$_3$Si-phenyl)$_2$C(2,7-$^t$Bu$_2$Flu)(Cp)HfCl$_2$ (15.0 g, 15.2 mmol) and toluene (125 mL). After stirring for 1 h, the mixture was filtered through a 4–8 μm frit then reduced to a solid invacuo. The product was extracted from the solids with hexane (250 mL) then filtered through a 0.45 μm filter. The crude product was crystallized from a minimum of hot hexane. Yield 8.9 g, 62%.

Synthesis of (p-Et$_3$Si-phenyl)$_2$C(Flu)(Cp)HfMe$_2$ (Catalyst B)

5. Synthesis of 6,6'-bis(p-Et$_3$Si-phenyl)fulvene

This fulvene was prepared similarly as described above in 1 and 2 on a smaller scale.

6. Synthesis of (p-Et$_3$Si-phenyl)$_2$C(Flu)(Cp)HfCl$_2$

Fluorenyl lithium (3.90 g, 22.6 mmol) was added to a cold (−30° C.) solution of crude 6,6'-bis(p-Et$_3$Si-phenyl)fulvene (10.35 g, 22.6 mmol) and ether (100 mL). After stirring for 2 h, the solvent was removed and the remaining solid slurried with pentane (100 mL), filtered, washed with additional pentane (2×100 mL) then dried invacuo to give p-Et$_3$Si-phenyl)$_2$C(FluH)(CpLi). Yield 6.41 g, 45%—assuming no ether present. 2 M BuLi in pentane (5.1 mL, 1 equiv.) was added to a slurry of the monoanion (6.4 g, 10.2 mmol) and ether (50 mL). The mixture was stirred overnight, cooled to −30° C. then treated with HfCl$_4$ (3.26 g, 1 equiv.). The mixture was warmed to room temperature, stirred for 8 h, filtered then washed with pentane (25 mL). The product was extracted from the orange solids with methylene chloride. Removing the solvent gave (p-Et$_3$Si-phenyl)$_2$C(Flu)(Cp)HfCl$_2$. Yield 6.15 g, 61%.

7. Synthesis of (p-Et$_3$Si-phenyl)$_2$C(Flu)(Cp)HfMe$_2$ (Catalyst B)

A 1.4 M solution of MeLi in ether (1.65 mL, 2.31 mmol) was added to a solution of (p-Et$_3$Si-phenyl)$_2$C(Flu)(Cp)HfCl$_2$ (1.0 g, 1.15 mmol) and toluene (25 mL). After stirring overnight, toluene was removed. The product was extracted from the solids with hexane then filtered through a 0.45 μm filter. Removing the solvent gave product. Yield 0.565 g, 59%.

As shown above preparation of the exemplary metallocenes required initial synthesis of 6,6'-bis(p-Et$_3$Si-phenyl)fulvene. This fulvene was prepared from the reaction of p-(Et$_3$Si)phenyllithium with ClC(O)NMe$_2$ then cyclopentadiene in an extension of a general procedure reported by H. Kurata and coworkers (*Tetrahedron Letters,* 1993, 34, 3445–3448). Further reaction of 6,6'-bis(p-Et$_3$Si-phenyl)fulvene with 2,7-$^t$Bu$_2$fluorenyl lithium yielded (p-Et$_3$Si-phenyl)$_2$C(2,7-$^t$Bu$_2$FluH)(CpLi). This monoanion displayed low solubility in pentane and was easily purified from contaminants. Subsequent treatment with BuLi then HfCl$_4$ gave the dichloride (p-Et$_3$Si-phenyl)2C(Flu)(Cp)HfCl$_2$, which was readily methylated. This methodology can easily be extended to prepare a wide variety of silyl substituted metallocenes.

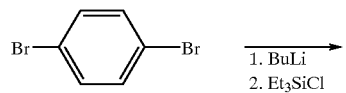

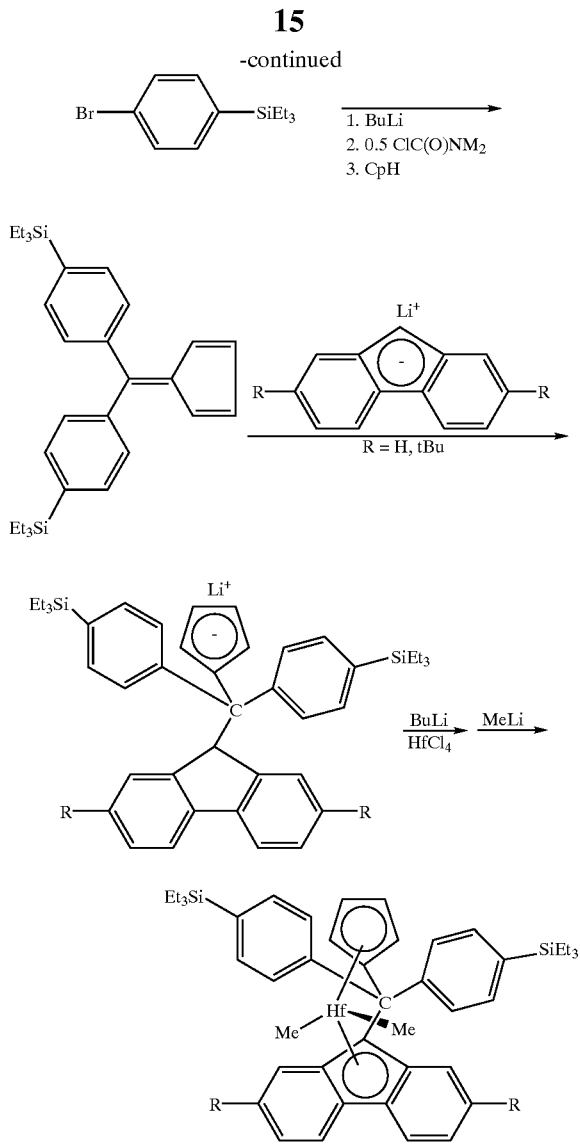

8. Solubility Studies

To a measured amount (typically $10^{-4}$ mol) of metallocene and a stirbar in a 20 mL scintillation vial was added dry hexane (ca. 2.65 mL). It was necessary to use a larger amount of A ($3 \times 10^{-4}$ mol) to determine its solubility. The mixture was stirred for ca. 1 h then an aliquot removed and filtered through a 0.45 μm filter (aliquot mass 2.2–2.5 g). The mass of the sample was recorded then the hexane removed with a slow nitrogen stream. Weight % solubility of the metallocene was determined as 100(mass solid remaining)/(mass filtered aliquot). See Tables below.

| Catalyst Symbol | Precatalyst Compound |
| --- | --- |
| A | $(p-Et_3Si-Ph)_2C(2,7-(^tBu)_2Flu)(Cp)HfMe_2$ |
| B | $(p-Et_3Si-Ph)_2C(Flu)(Cp)HfMe_2$ |
| C (Comp) | $Ph_2C(2,7-(^tBu)_2Flu)(Cp)HfMe_2$ |
| D (Comp) | $Ph_2C(Flu)(Cp)HfMe_2$ |

SOLUBILITY TABLE

| | Initial Mixture (Calculated) | | | Filtered Aliquot | | |
| --- | --- | --- | --- | --- | --- | --- |
| Precatalyst | Precat | soln. mass | max. wt % | soln. mass | Precat | wt % |
| A | 0.0905 | 2.6603 | 3.40% | 2.3715 | 0.0793 | 3.3%[1] |
| A | 0.2828 | 2.7653 | 10.23% | 2.521 | 0.2434 | 9.65%[3] |
| A | 0.2844 | 2.8224 | 10.08% | 2.5557 | 0.2338 | 9.15%[3] |
| C(Comp) | 0.0705 | 2.6191 | 2.69% | 2.236 | 0.0476 | 2.1% |
| C(Comp) | 0.1049 | 2.6805 | 3.91% | 2.383 | 0.0445 | 1.9% |
| B | 0.0848 | 2.6483 | 3.20% | 2.3898 | 0.0511 | 2.1% |
| D(Comp) | 0.0594 | 5.1069 | 1.16% | 3.7209 | 0.0045 | 0.1%[2] |
| D(Comp) | 0.0612 | 12.1902 | 0.50% | 11.5233 | 0.0079 | <0.07%[2] |

[1]Control run using a fully dissolved catalyst A as determined by visual observation indicated ca. 3% error between the calculated "max wt %" and the actual measured wt % after filtering.
[2]An upper limit of D solubility is 0.07% since an increase in hexane did not proportionally increase the amount of solids remaining.
[3]Average A solubility is 9.4%.

Example 9a

Polymerization Example

Under a nitrogen atmosphere, a 1 L autoclave was charged with hexane (460 mL) and trioctylaluminum (0.04 mL of a 25 wt % solution in hexane diluted with hexane (10 mL)). The autoclave was stirred at ca. 1000 rpm, heated to 113.6±0.4° C. (P=47.2±0.5 psig) then pressurized with propylene to 103.3±0.3 psig then ethylene to 251 psig. Ethylene flow into the reactor was allowed during the copolymerization. A $3.94 \times 10^{-5}$ M of hexane soluble activator $[((3,5-(Et_3Si)_2-Ph)_3C]+[B(C_6F_5)_4]^-$ solution in hexane (20 mL, 0.79 μmol)(hexane soluble activator) was pumped into the reactor. Then a $3.97 \times 10^{-5}$ M $(p-Et_3Si-Ph)_2C(2,7-^tBu_2Flu)(Cp)HfMe_2$ solution in hexane was added at a variable rate sufficient to maintain ethylene flow into the reactor at <1 L/min and the reaction exotherm <0.5° C. The mean temperature during the polymerizations was 113.7±0.5° C. Ethylene uptake was monitored with a calibrated mass-flow transducer. The polymerization was halted after ca. 12 g of polymer was produced. The reactor was vented and cooled. The polymer solution was poured from the reactor into a large beaker. The reactor was rinsed with additional hot hexane (ca. 500 mL). The polymer solutions were combined then treated with a stream of nitrogen to remove hexane; the polymer was further dried under vacuum at 80° C. Polymerization data is given in table 1.

Example 9b

The procedure of 9a. was repeated.

Example 9c

The procedure of 9a. was repeated.

Example 10a

The general procedure of 9a. was followed with an activator substitution: The reactor was charged with solvent, $AlOct_3$ then a slurry of the activator compound $PhNMe_2H^+ B(C_6F_5)_4^-$ (5 mg, 6.2 μmol) in hexane (20 mL) then heated to 113.5° C. and charged with propylene and ethylene. Then the precatalyst was added to this mixture.

Example 10b

The procedure of 10a. was repeated using a slurry of the activator compound $[PhNMe_2H]^+ [B(C_6F_5)_4]^-$ (1.2 mg, 1.5 μmol) in hexane (20 mL).

Example 11a

Comparative Example

The general procedure of 9a. was followed with an activator substitution: A $1.5 \times 10^{-4}$ M $B(C_6F_5)_3$ solution in hexane (25 mL, 3.78 μmol) was pumped into the reactor in place of the R1 solution used in example 9a. Due to low activity, the polymerization was halted after 2.92 g of polymer was prepared.

Example 11b

Comparative Example

The procedure of 11a. was repeated. Due to low activity, the polymerization was halted after 0.7 g of polymer was prepared.

Example 12a

Polymerization Example

The procedure of example 9a was followed with a precatalyst substitution: A mixture of (p-Et$_3$Si—Ph)$_2$C(Flu)(Cp)HfMe$_2$ (50 mg, 60.1 μmol) and hexane (2.5 g) was stirred for 30 min then allowed to sit for 10 min. An aliquot (150 μL) of the mixture was removed and diluted with hexane 80 mL. This precatalyst solution was added to a reactor as described in example 9a.

Example 12b

Polymerization Example

The procedure of example 12a was repeated using the same precursor.

Example 12c

Comparative Example

The procedure of example 9a was followed with a precatalyst substitution: A mixture of catalyst D above ((Ph)$_2$C(Flu)(Cp)HfMe$_2$)(50 mg, 82.9 μmol) and hexane (2.5 g) was stirred for 30 min then allowed to sit for 10 min. An aliquot (150 μL) of the mixture was removed and diluted with hexane 80 mL. This precatalyst solution was added to a reactor as described in example 9a.

Example 12d

Comparative Example

The procedure of example 12c was repeated using the same mixture.

TABLE 1

POLYMERIZATION RESULTS

| Ex # | μmol Cat | μmol Act | Polymer mass | Wt % C$_3$ (IR) | M$_w$ (LS) | M$_w$/M$_n$ (DRI) |
|---|---|---|---|---|---|---|
| 9a | 0.13 | 0.79 | 12.41 | 32 | 629427 | 1.85 |
| 9b | 0.11 | 0.79 | 11.79 | 31 | 647659 | 1.7 |
| 9c | 0.12 | 0.79 | 10.33 | 32 | 575956 | 1.9 |
| 10a | 0.056 | 6.2 | 11.42 | 32 | 557884 | 1.95 |
| 10b | 0.094 | 1.5 | 11.28 | 32.5 | 589690 | 1.9 |
| 11a(Comp) | 0.70 | 3.8 | 2.92 | 32 | 573913 | 1.9 |
| 11b(Comp) | 0.893 | 3.8 | 0.7 | a | a | a |
| 12a | 0.183$^b$ | 0.79 | 12.60 | 31 | 510697 | 2.0 |
| 12b | 0.183$^b$ | 0.79 | 6.77 | 33.5 | 492952 | 2.0 |
| 12c(Comp) | c | 0.79 | 0.4 | a | a | a |
| 12d(Comp) | c | 0.79 | 0 | a | a | a |

(a) not measured (b, c) (p-Et$_3$Si-Ph)$_2$C(Flu)(Cp)HfMe$_2$ was completely soluble; Ph$_2$C(Flu)(Cp)HfMe$_2$ had little solubility under these conditions (c) μmol unknown.

The comparison presented in example 12 above illustrates that the productivity of a polymerization is proportional to the concentration of the catalyst precursor compound feed solution. Catalyst B is more soluble that catalyst D in hexane. Thus, the mixtures of B in hexane result in and increase in polymerization productivity, 6.8 to 12.6 g polymer, as compared to that of catalyst D, at 0–0.4 g polymer.

Example 13

Ethylene/Octene Copolymerizations

Under a nitrogen atmosphere, a 500 mL autoclave was charged with hexane (250 mL), triisobutylaluminum (0.2 mL of a 25.2 wt % solution in heptane diluted with toluene (5 mL)) and 1-octene (18 mL, 115 mmol). The autoclave was stirred at ca. 1500 rpm, heated to 140.1° C. (P=75.7 psig) then pressurized with ethylene to 265.6±1 psig. Ethylene flow into the reactor was allowed during the copolymerization. A solution of precatalyst (40–50 μmol), PhNMe$_2$H$^+$ B(C$_6$F$_5$)$_4^-$ (1 equiv.) and toluene (100 mL) was added to the stirred mixture over 30 min. at a variable rate sufficient to obtain 12–15 g isolated copolymer with an exotherm of less than 1.5° C., typically less than 1° C. The polymer was precipitated with 2-propanol (1.5 L), isolated, then dried under vacuum at 80° C. See Table below.

| Precatalyst | Precat. used (μMol) | Copolymer Yield (g) | Mol % octene | M$_w$ (DRI) | M$_w$/M$_n$ (DRI) | M$_w$ (LS) |
|---|---|---|---|---|---|---|
| A | 2.1 | 12.18 | 6.4 | 195692 | 3.12 | 225188 |
| A | 1.5 | 12.79 | 6.1 | 190771 | 2.30 | 210680 |
| A | 2.2 | 13.82 | 6.4 | 207125 | 2.30 | 248319 |
| A | 2.4 | 14.98 | 6.1 | 219112 | 2.43 | 254290 |
| B | 5.0 | 12.40 | 7.3 | 150225 | 2.22 | 177924 |
| B | 4.4 | 12.98 | 7.6 | 163758 | 2.22 | 194604 |
| D | 5.8 | 12.49 | 9.5 | 140664 | 2.25 | 173690 |
| D | 4.2 | 12.25 | 7.5 | 154822 | 2.20 | 189865 |

Molecular weights determined from GPC using a differential refractive index (DRI) or light scattering (LS) detector.

The solubility data above exhibits significant and unexpected increase in solubility for catalyst of the invention as compared with those of the prior art. The polymerization data illustrates equivalent activities such that the benefits of increased solubility in aliphatic solvents can be achieved without sacrifice of the levels of productivity previously achieved with the prior art catalysts.

Example 14

Continuous High Temperature Solution Process

The following polymerization reactions were performed in a stirred, liquid filled 2 L jacketed steel reactor equipped to perform continuous insertion polymerization in presence of an inert $C_6$ hydrocarbon (naphta) solvent at pressures up to 120 bar and temperatures up to 240° C. The reactor was typically stirred at 1000 rpm during the polymerization. The reaction system was supplied with a thermocouple and a pressure transducer to monitor changes in temperature and pressure continuously, and with means to supply continuously purified ethylene, 1-octene, and solvent. In this system, ethylene dissolved in the hydrocarbon solvent, 1-octene, tri-n-octyl aluminum (TOA) used as a scavenger, and optionally $H_2$, are pumped separately, mixed, and fed to the reactor as a single stream, refrigerated to below 0° C. The transition metal component (TMC) was dissolved in a solvent/toluene mixture (9/1 vol/vol) whereas the non-coordinating anion (NCA) activator was dissolved in toluene/solvent mixture (1/1 vol/vol). Both components were pumped separately, mixed at ambient temperature, and cooled to below about 0° C. prior to entering the reactor. The reactor temperature was set by adjusting the temperature of an oil bath used as a reservoir for the oil flowing through the reactor wall jacket. Next, the polymer molecular weight (MW) or MI was controlled independently by adjusting the ethylene conversion (% $C_2$) in the reactor via the catalyst flow rate. Finally, the polymer density was controlled by adjusting the ethylene/1-octene weight ratio in the feed. See Tables below.

4. The organometallic compound of claim 3 wherein said catalyst compound is a hafnium organometallic compound and said substituted Group 14 atom is a carbon atom.

5. The organometallic compound of claim 4 wherein said compound is a biscyclopentadienyl hafnium organometallic compound having i) at least one unsubstituted cyclopentadienyl or indenyl ligand, ii) one aromatic fused-ring substituted cyclopentadienyl ligand.

6. The organometallic compound of claim 4 wherein said aromatic fused-ring substituted cyclopentadienyl ligand is a substituted or unsubstituted fluorenyl ligand.

7. The organometallic compound of claim 6 wherein said unsubstituted cyclopentadienyl ligand or aromatic fused-ring substituted cyclopentadienyl ligand is an unsubstituted cyclopentadienyl ligand.

8. The organometallic compound of claim 7 wherein said hafnium compound is selected from the group consisting of di(p-trimethylsilyl-phenyl)methylene(cyclopentadienyl)(fluorenyl)hafnium dimethyl, di(p-trimethylsilyl-phenyl)methylene (cyclopentadienyl)(2,7-dimethyl-9-fluorenyl) hafnium dimethyl and di(p-trimethylsilyl-phenyl)methylene (cyclopentadienyl)(2,7-di-tert-butyl-9-fluorenyl)hafnium dimethyl, di(p-triethylsilyl-phenyl)methylene

| | | | | Polymerization Conditions | | | | | | |
|---|---|---|---|---|---|---|---|---|---|---|
| Exp 14 # | Cat | Act | Cat. Feed (mg/hr) | Act. Feed (mg/hr) | Alkyl-Al (mmol/l) | Rt (min) | Temp. (° C.) | Press. (bar) | Solvent (kg/hr) | $C_2$ Feed (kg/hr) | $C_8$ Feed (kg/hr) |
| a) | A | $(F_5C_6)_4B^{-(1)}$ | 3.3 | 2.7 | 0.015 | 7.2 | 190 | 85.8 | 5.5 | 1.16 | 0.53 |
| b) | A | $(F_7C_{10})_4B^{-(2)}$ | 5.2 | 5.8 | 0.015 | 7.0 | 196 | 85.8 | 5.7 | 1.17 | 0.54 |

(1)[N,N-dimethylanilinium][tetrakis(perfluorophenyl)boron]
(2)[N,N-dimethylanilinium][tetrakis(heptafluoronaphthyl)boron]

| | | | | Product Analysis | | | | | |
|---|---|---|---|---|---|---|---|---|---|
| Exp 14 # | $C_2$ Conv (%) | $C_8$ Conv (%) | Prod Rate (kg/hr) | Cat. Prod. (kgPE/mg Cat) | MI (dg/min) | MIR (I21/I2) | Density (kg/m$^3$) | $C_8$ Incorp. (wt %) | $M_w$ (kg/mol) | PDI ($M_w/M_n$) |
| a) | 84 | 48 | 1.46 | 440 | 0.84 | 39 | 903 | 17 | 95 | 2.3 |
| b) | 85 | 45 | 1.47 | 280 | 0.96 | 42 | 909 | 16 | 89 | 2.2 |

What is claimed is:

1. A Group 4 organometallic compound comprising two ancillary monoanionic ligands, each of which independently may be substituted or unsubstituted, wherein the ligands are bonded by a covalent bridge containing a substituted single Group 14 atom, the substitution on said Group 14 atom comprising aryl groups at least one of which contains at least one hydrocarbylsilyl substituent group.

2. The compound of claim 1 wherein said hydrocarbylsilyl substituent has the formula $R_n"SiR'_{3-n}$, where each R' is independently a $C_1$–$C_{20}$ hydrocarbyl, hydrocarbylsilyl, hydrofluorocarbyl substitutent, R" is a $C_1$–$C_{10}$ linking group between Si and the aryl group, and n=0 or 1.

3. The organometallic compound of claim 2 wherein each R' is a linear $C_1$–$C_6$ linear or branched alkyl substituent.

(cyclopentadienyl)(fluorenyl)hafnium dimethyl, di(p-triethylsilyl-phenyl)methylene(cyclopentadienyl)(2,7-dimethyl-9-fluorenyl)hafnium dimethyl, di(p-triethylsilyl-phenyl)methylene (cyclopentadienyl)(2,7-di-tert-butyl-9-fluorenyl)hafnium dimethyl, (p-triethylsilyl-phenyl)(p-tert-butylphenyl)methylene(cyclopentadienyl)(fluorenyl) hafnium dimethyl, (p-triethylsilyl-phenyl))(p-n-butylphenyl)methylene(cyclopentadienyl)(2,7-dimethyl-9-fluorenyl)hafnium dimethyl, (p-trimethylsilylphenyl)(p-n-butylphenyl)methylene(cyclopentadienyl)(2,7-di-tert-butyl-9-fluorenyl)hafnium dimethyl, and (p-triethylsilyl-phenyl)(p-n-butylphenyl)methylene (cyclopentadienyl)(2,7-dimethyl-9-fluorenyl)hafnium dimethyl.

* * * * *